United States Patent [19]

Kuhlmann

[11] Patent Number: 4,696,955
[45] Date of Patent: Sep. 29, 1987

[54] X-RAY OPAQUE DENTAL FILLING COMPOSITION-BROMINATED AROMATIC DI-METHACRYLIC ESTER POLYMERIZABLE COMPONENT

[75] Inventor: Werner Kuhlmann, Mainz-Hechtsheim, Fed. Rep. of Germany

[73] Assignee: Blendax-Werke R. Schneider GmbH & Co., Mainz, Fed. Rep. of Germany

[21] Appl. No.: 669,846

[22] Filed: Nov. 9, 1984

[30] Foreign Application Priority Data

Nov. 25, 1983 [DE] Fed. Rep. of Germany ....... 3342601

[51] Int. Cl.$^4$ .......................... A61K 6/08; A61C 8/00
[52] U.S. Cl. .................................. 522/77; 433/199.1; 433/201.1; 433/228.1; 522/14; 522/103; 522/181; 523/116; 523/117; 526/292.3; 526/292.4
[58] Field of Search .................. 523/116, 117; 526/292.3, 292.4; 522/181, 14, 77

[56] References Cited

U.S. PATENT DOCUMENTS

| | | | |
|---|---|---|---|
| 3,345,401 | 10/1967 | May | 526/313 |
| 3,709,866 | 1/1973 | Waller | 522/181 |
| 3,715,331 | 2/1973 | Molnar | 523/120 |
| 4,077,859 | 3/1978 | Costanza | 526/292.4 |
| 4,107,845 | 8/1978 | Lee | 523/116 |
| 4,150,012 | 4/1979 | Joos | 523/116 |
| 4,297,266 | 10/1981 | Ibsen | 523/116 |
| 4,302,376 | 11/1981 | Walkowiak et al. | 106/35 |
| 4,442,239 | 4/1984 | Tsunekawa et al. | 523/116 |

FOREIGN PATENT DOCUMENTS

| | | |
|---|---|---|
| 142921 | 5/1985 | European Pat. Off. . |
| 3120965 | 2/1982 | Fed. Rep. of Germany . |
| 57-154114 | 9/1982 | Japan . |
| 58-72102 | 4/1983 | Japan . |
| 82/01006 | 4/1982 | World Int. Prop. O. .......... 523/117 |
| 1483816 | 8/1977 | United Kingdom . |
| 747850 | 7/1980 | U.S.S.R. . |

Primary Examiner—A. Lionel Clingman
Attorney, Agent, or Firm—Birch, Stewart, Kolasch & Birch

[57] ABSTRACT

Dental restoration materials with improved properties, particularly X-ray opacity and polishability, are obtained, if they contain fillers and polymerizable compounds consisting in total or in part of one or more compounds of the general formula

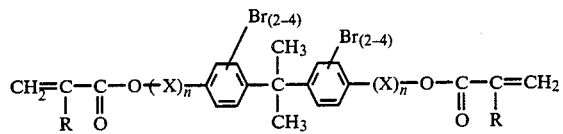

where R represents H or a methyl group, X is representing a $CH_2-CH_2-O-$, $CH_2-CH_2-CH_2-O-$, or $$CH_2-CH-CH_2-O- \text{ group,}$$
$$\phantom{CH_2-C}OH$$

and n means 0 to 3.

24 Claims, No Drawings

X-RAY OPAQUE DENTAL FILLING COMPOSITION-BROMINATED AROMATIC DI-METHACRYLIC ESTER POLYMERIZABLE COMPONENT

The present invention relates to a dental restoration material for the filling of tooth cavities showing improved properties, particularly an improved X-ray opacity.

During the last years particularly dental filling materials consisting of fillers and polymerizable compounds, the so-called "composites", have gained increased importance in dental medicine. These products can be handled easily by the dentist, are usually well tolerated without any irritation by the patient, ensure an aesthetically attractive appearance of the filling, and offer the possibility to move away from amalgam filling materials which have been criticized for physiological reasons.

Among the required properties to be met by such "composites", those relating to visibility of the filling under the influence of X-rays, i.e. X-ray opacity, and those relating to the polishability of the filling surfaces are particularly imporatant. However, the fulfillment of these requirements with the known "composites" raises problems: On one hand, if a well polishable filler combination, usually consisting of a major proportion of finely divided silica and a very minor proportion of barium silicate glass particles, is used, the result may be a good polishability, but an insufficient X-ray opacity; on the other hand, if the proportion of X-ray opaque filler having relatively high particle diameters is increased, a sufficient polishability of the filling made on the basis of this composition is not obtained.

The present invention solves this problem in an extremely advantageous way by using a dental restoration material capable of being polymerized in a tooth cavity under physiologically tolerable conditions which contains polymerizable compounds, fillers, polymerization catalysts, and/or accelerators and optionally other substances normally used in such materials containing at least one or more compounds of the general formula

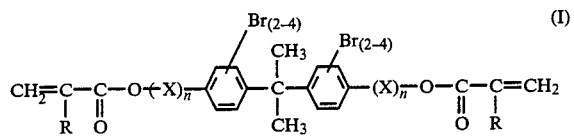

where R represents H or a methyl group, X is representing a $CH_2-CH_2-O-$, $CH_2-CH_2-CH_2-O-$, or $CH_2-CH-CH_2-O-$ group,
$\quad\quad\quad\quad\quad\quad\quad\quad\quad\quad\quad\quad\quad\quad\quad |$
$\quad\quad\quad\quad\quad\quad\quad\quad\quad\quad\quad\quad\quad\quad\;\, OH$ and n means 0 to 3.

The application of these compounds even in combination with high proportions of a very finely divided filling material, particularly silica-gels with average particle diameters between approx. 20 and approx. 200 nm, which are used for the preparation of well polishable filling materials, after curing will lead to a filling with a sufficient X-ray opacity.

The use of these monomers according to the general formula (I) is particularly advantageous in the preparation of so-called light-curing "composites", i.e. materials which are applied as "one-phase compositions", usually containing a photopolymerization initiator and cured by irradiation; however, the use of these monomers also is possible in so-called self-curing "composites" applied as "two-phase compositions" kept separately until use.

According to a preferred embodiment of the invention, the proportion of the brominated monomers according to the general formula (I) is between approx. 30 to approx. 90% by weight, preferably approx. 55 to 85, particularly 60 to 75% by weight, of the total amount of the polymerizable compounds used in the dental restoration material.

These polymerizable compounds are contained in the dental restoration materials according to the invention usually in an amount between approx. 15 and approx. 50, preferably approx. 20 to approx. 40% by weight, calculated to the total composition of the restoration material.

Consequently, the rest of the material consists of approx. 50 to approx. 85, preferably approx. 60 to approx. 80% by weight, calculated to the total composition, of a filler or a filler mixture with an average particle diameter of less than 30 micrometers and approx. 0.05 to approx. 2.0% by weight of at least one polymerization initiator and/or polymerization accelerator and optionally additional components normally used in such compositions.

According to a preferred embodiment of the invention, the brominated polymerizable compound (I) is a compound of the following formula

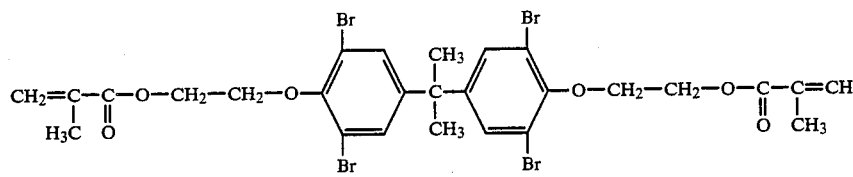

This compound may be prepared by ethoxylation of the corresponding 2,2-di-(3,5-dibromo-4-hydroxyphenyl)propane and subsequent esterification of the ethoxylation product with methacrylic acid.

Analogously, the corresponding hexa- and octabromo compounds and monoethyoxy compounds of the structure

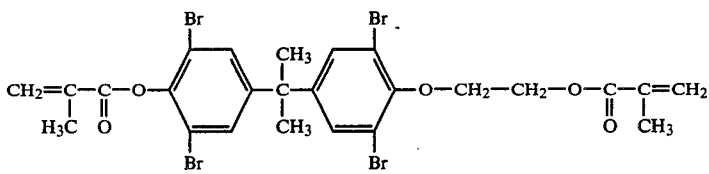

(III)

or triethoxy compounds, resp., and, in case of condensation of brominated bis(hydroxyphenyl)propane with propylene oxide, also the corresponding propoxylates are prepared.

Compounds of this type and their preparation are known per se and described, e.g., in DE-A No. 2,648,969, particularly in Example 6 thereof, where they are used for the preparation of plastic materials with reduced inflammability.

The preparation of these dimethacrylates may also be effected according to the procedure described in JP-A No. 5,795,941 (Chemical Abstracts, Vol. 98, No. 34239y) as well as in JP-A No. 8,293,931 (Chemical Abstracts, Vol. 97, 183393a).

Another preferred monomer derives from the reaction product of Bisphenol A and glycidyl methacylate and has the formula

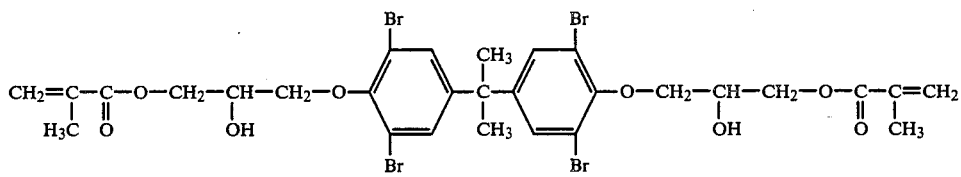

(IV)

Such compounds are already known from SU-A No. 747,850. There they are copolymerized together with other monomers, particularly methyl methacrylate, to improve heat resistance of plastics; these copolymers are reported to have self-extinguishing properties.

Also DE-A No. 2,747,947 describes the use of corresponding monomers, namely di-(3-methacryloxy-2-hydroxypropyl)-ether and di-(2-methacryloxyethyl)ether of tetrabromo-Bisphenol A in photopolymerizable compositions, which are used as photo-resists and solder masks.

Finally, DE-A No. 3,120,965 reveals copolymerizates which can be used for the production of lenses with a high refraction index, and excellent transparency and fireproof quality, containing brominated monomers according to the general formula (I). These brominated monomers can be used in the dental restoration materials according to the invention.

In view of this prior art and the possiblities of use for these brominated Bisphenol A-methacrylates described therein, it was highly surprising for the expert that these substances may be used as bonding agents in dental restoration materials resulting in fillings with optimal properties as regards to X-ray opacity and polishability, which could not be obtained with the compositions used up to now for this purpose.

As already mentioned, the restoration materials according to the invention may contain the monomers of the general formula (I) as sole bonding agents.

However, it has been found to be advantageous to use them in admixtures with additional (meth)acrylic acid esters usually known for this purpose. Such esters are particularly alkanediol dimethacrylates such as 1,6-hexanediol dimethacrylate, tri-and/or tetraethyleneglycol dimethyacrylate, 1,4-butanediol dimethacrylate, trimethylol propane di- and -trimethacrylate, bis-(2-methacryloxyethyl)-phthalate, -isophthalate or -terephthalate, reaction products of diisocyanates and simple hydroxyalkyl methacrylates as described e.g. in DE-A No. 2,312,559, reaction products of substituted bisphenols, particularly Bisphenol A and glycidyl methacrylate (Bis-GMA), adducts of (di-)isocyanates and 2,2-propanebis-3-(4-phenoxy)-1,2-hydroxypropane-1-methacrylate according to U.S. Pat. No. 3,629,187, the adducts of methacroyl alkyl ethers, alkoxy benzenes and/or alkoxy cycloalkanes and diisocyanates described in EP-A No. 44,352, (meth)acrylic acid esters with carbamic acid groups known from U.S. Pat. No. 3,425,988 as well as reaction products of diisocyanates and hydroxyalkyl diacrylates and -methacrylates described in DE-A No. 2,079,297, and any other polymerizable compounds already suggested for this purpose.

As already explained, the preferred percentage of brominated methacrylic acid compounds of the general formula (I) if from 30 to 90, preferably 55 to 85, particularly 60 to 75% by weight of all polymerizable compounds present in the dental restorative composition.

Generally, the filler content will be more than 50% by weight of the total composition.

The filling materials used may be X-ray transparent or X-ray opaque. In any case, due to the properties of the brominated monomers, the percentage of the X-ray opaque material, usually having a higher average particle diameter and thus reducing the polishability of the filling, is reduced to such a degree that sufficient polishability of the cured filling is obtained, maintaining at the same time X-ray opacity.

It is even possible to omit X-ray opaque fillers in the dental restorative compositions according to the invention provided the percentage of brominated monomers is high enough to scure X-ray opacity.

Examples of appropriate fillers are particularly the various silica modifications such as colloidal (i.e., precipitated or pyrogenic) silica-gels, glass (pulverized glass), borosilicate glass, and other glasses such as quartzite, cristobalite and others, glass ceramics fillers, barium aluminum silicate, lithium aluminum silicate, and glasses containing rare-earth elements such as lanthanum or zirconium.

Appropriate fillers are for example described in U.S. Pat. Nos. 3,801,344, 3,808,170, and 3,975,203 as well as in DE-A No. 2,347,591.

To increase the affinity between bonding agents and fillers the latter can be silanized in a known way.

The particle sizes of the fillers to be used are usually between approx. 0.01 and approx. 30 micrometers.

A preferred filler is a combination of barium aluminum silicate glass with an average particle size of between approx. 3 and 10 micrometers and a finely divided colloidal silica with an average particle diameter of between approx. 30 and 100 nm. Preferably, the major part of this mixture consists of finely divided silica, for example in the ratio 2:1, in admixture with barium silicate glass.

Appropriate fillers are also the highly silanized silicas described in EP-A No. 60,911, and mixtures of amorphous and crystalline fillers known from U.S. Pat. No. 4,388,069.

"Composites" are existing in two different modifications, either as two-phase preparations, one phase containing a polymerization initiator, for example a peroxide, and the other phase containing an accelerator for this peroxide, for example an amine; in such cases the two phases are brought together immediately before filling the tooth and the polymerization takes place in the open cavity to be filled, preferably being provided with a bonding material.

The other modification of a "composite", which according to the invention is preferred, is a one-phase preparation which polymerizes under the influence of light and usually contains a photopolymerization initiator and preferably also an accelerator.

Such photopolymerization intiators are well-known; they are preferably carbonyl compounds, particularly benzil and benzil derivatives such as 4,4-oxydibenzil or other dicarbonyl compounds, for example diacetyl, 2,3-pentanedione or metal carbonyls, quinone, particularly camphoroquinone, and their derivatives.

Characteristical photopolymerization intitiators for dental filling materials are, for example, described in DE-A No. 2,126,419.

The preferred percentage of photopolymerization initiators is from approx. 0.01 to approx. 1.0% by weight of the total composition. Preferably, these light-curable dental filling materials also contain polymerization accelerators.

These are particularly the various amines such as p-toluidine, dimethyl-p-toluidine, dimethyl- and diethylaminoethyl methacrylate, trialkylamines, polyamines, dialkyl barbituric acids and sulfimides, preferably in an amount of between approx. 0.01 and 2.5% by weight of the total composition.

If the dental restoration material according to the invention is not supposed to be light-curable and thus to be present in two phases being kept separately until use, one of these phases usually contains a polymerization initiator. These are mostly peroxides which decompose under formation of radicals to initiate polymerization. Appropriate peroxides are, for example, aryl peroxides such as benzoyl peroxide, cumene hydroperoxide, carbamide peroxide, tert.-butyl hydroperoxide or perbenzoate and silyl peroxides, in amounts from preferably 0.01 to 5, particularly approx. 0.5 to approx. 2.5% by weight of the total composition.

If one phase of the two-phase material contains a polymerization initiator, an accelerator of the above described type, preferably an amine, should be added to the other phase.

To improve the natural appearance of the filled tooth surfaces, composite materials may contain dyestuffs in small amounts.

Additionally, the use of small amounts of UV-stabilizers is possible. Appropriate stabilizers are hydroquinone, p-benzoquinone, p-butyl hydroxy toluene, propyl gallate, etc.

The following examples shall explain the invention:

EXAMPLE 1

| | |
|---|---|
| Silanized pyrogenic silica-gel of the type Aerosil ® (average particle diameter 40–50 nm) | 43.7 (parts by weight) |
| Silanized barium silicate glass (average particle diameter 3–10 μm) | 25.6 |
| 1,6-hexanediol dimethacrylate | 10.7 |
| Isopropylidene bis-[2-(3,5-dibromo-4-phenoxy)ethyl]methacrylate | 19.5 |
| Dimethyl aminoethyl methacrylate | 0.3 |
| Camphoroquinone | 0.1 |
| Ethyl benzoin | 0.1 |
| UV-stabilizers, dyestuffs optical brightener | q.s. |

After light-curing a highly polishable X-ray opaque material was obtained.

When the isopropylidene bis-[2-(3,5-dibromo-4-phenoxy)ethyl]methacrylate was substituted by the non-brominated compound usually used in composites a polishable but not X-ray opaque filling was obtained.

EXAMPLE 2

| | |
|---|---|
| Silanized pyrogenic silica-gel of the type Aerosil ® (average particle diameter 60 nm) | 55.4 (parts by weight) |
| 1,6-hexanediol dimethacrylate prepolymerizate | 6.0 |
| Triethyleneglycol dimethacrylate | 8.0 |
| Isopropylidene bis-[2-(3,5-dibromo-4-phenoxy)ethyl]methacrylate | 30.0 |
| Diethyl aminoethyl methacrylate | 0.4 |
| Camphoroquinone | 0.1 |
| Ethyl benzoin | 0.1 |
| UV-stabilizer, pigments, optical brightener | q.s. |

After light-curing a highly polishable, X-ray opaque filling was obtained.

EXAMPLE 3

| | |
|---|---|
| Silanized colloidal silica-gel (average particle diameter 50–100 nm) | 42.8 (parts by weight) |
| Silanized quartz powder (average particle diameter 3–8 μm) | 12.5 |
| Triethyleneglycol dimethacrylate | 15.5 |
| Isopropylidene bis-[(2-hydroxy-3-(3,5-dibromo-4-phenoxy)propyl]metharylate | 28.5 |
| Camphoroquinone | 0.15 |
| Dimethyl aminoethyl methacrylate | 0.4 |
| Ethyl benzoin | 0.15 |
| UV-absorber, optical brightener | q.s. |

After light-curing of this composition a highly polishable X-ray opaque filling was obtained.

When the brominated monomer was substituted by the same amount of the basic material isopropylidene bis-[2-hydroxy-3-(4-phenoxy)propyl]methacrylate a non-X-ray opaque filling material was obtained.

EXAMPLE 4

|  | Component A | Component B |
|---|---|---|
| Silanized, pyrogenic silica-gel (average particle diameter 30–60 nm) | 45.0 | 45.0 (parts by weight) |
| Silanized barium silicate glass (average particle diameter 5–10 μm) | 25.0 | 25.0 |
| Triethylene glycol dimethacrylate | 10.4 | 10.4 |
| Isopropylidene bis-[2-(3,5-dibromo-4-phenoxy)ethyl] methacrylate | 19.0 | 19.0 |
| N,N—dihydroxyethyl-p-toluidine | 0.5 | |
| Benzoyl peroxide | | 0.4 |
| UV-stabilizers, dyestuffs | q.s. | q.s. |

After curing a highly polishable, X-ray opaque product was obtained.

I claim:

1. A dental restoration material capable of being polymerized in a tooth cavity under physiologically tolerable conditions, comprising:
   between approximately 15 and approximately 50 percent by weight of polymerizable compounds, said polymerizable compounds containing an effective amount to impart X-ray opacity to the composition of one or more brominated monomers of the formula:

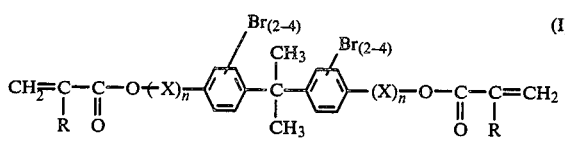

where R represents hydrogen or a methyl group, X represents a $-CH_2-CH_2-O-$, $-CH_2CH_2CH_2-O-$ or $-CH_2-CH-CH_2-O-$
                |
               OH group and n is 0 to 3; and
a silanized dental filler.

2. The dental restoration material of claim 1, which contains a compound of the formula:

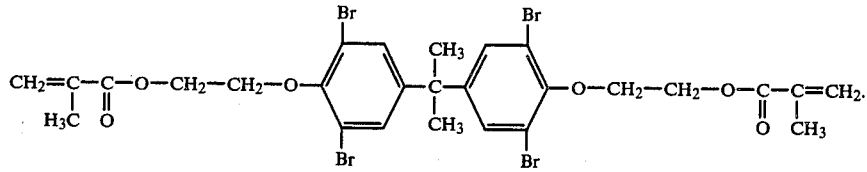

3. The dental restoration material of claim 1, which contains a compound of the formula:

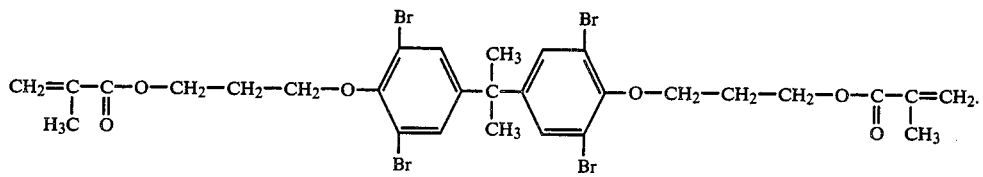

4. The dental restoration material of claim 1, which contains a compound of the formula:

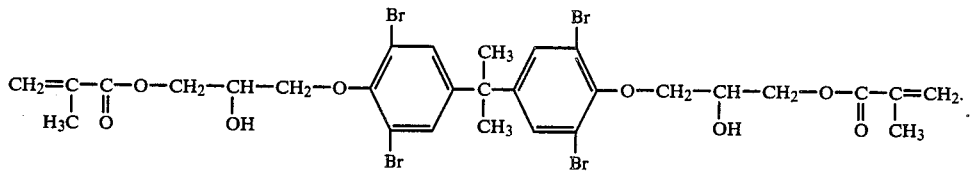

5. The dental restoration material of claim 1, wherein said brominated monomers of the formula (I) are present in an amount of 30 to 90% by weight based on the total weight of the polymerizable compounds.

6. The dental restoration material of claim 2, wherein said brominated monomers of the formula (I) are present in an amount of 30 to 90% by weight based on the total weight of polymerizable compounds.

7. The dental restoration material of claim 3, wherein said brominated monomers of the formula (I) are present in an amount of 30 to 90% by weight based on the total weight of polymerizable compounds.

8. The dental restoration material of claim 4, wherein said brominated monomers of the formula (I) are present in an amount of 30 to 90% by weight based on the total weight of polymerizable compounds.

9. The dental restoration material of claim 1, wherein said brominating monomers of the formula (I) are present in an amount of 55 to 85% by weight based on the total weight of polymerizable compounds.

10. The dental restoration material of claim 1, which is a light-curable composition.

11. The dental restoration material of claim 10, which contains at least one silanized dental filler having a particle size of between approximately 0.01 and approximately 30 micrometers and at least one polymerization accelerator.

12. The dental restoration material of claim 1, which is a one-part, light-curable composition.

13. The dental restoration material of claim 11, which is a one-part, light-curable composition.

14. A photopolymerizable dental restoration material capable of being polymerized in a tooth cavity under physiologically tolerable conditions, comprising:

approximately 15 to approximately 50% by weight of polymerizable compounds containing an effective amount to impart X-ray opacity to the composition of at least one brominated monomer of the formula:

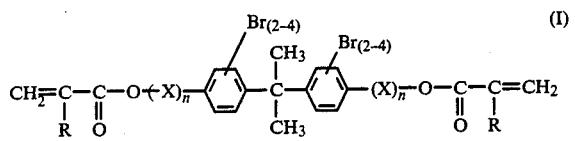

wherein R represents hydrogen or a methyl group, X represents a $-CH_2-CH_2-O-$, $-CH_2-CH_2-CH_2-O-$ or

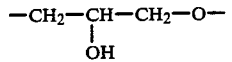

group and n is 0 to 3;

approximately 50 to approximately 85% by weight of at least one silanized dental filler with an average particle diameter of less than 30 micrometers; and approximately 0.05 to approximately 2.0% by weight of at least one polymerization initiator, polymerization accelerator or mixtures thereof.

15. The dental restoration material of claim 14, wherein 30 to 90% by weight of the total weight of said polymerizable compounds are said brominated monomers of the formula, (I).

16. The dental restoration material of claim 14, wherein 55 to 85% by weight of the total weight of said polymerizable compounds are said brominated monomers of the formula (I).

17. The dental restoration material of claim 15, wherein 60 to 75% by weight of the total weight of said polymerizable compounds are said brominated monomers of the formula (I).

18. The dental restoration material of claim 14, wherein polymerizable compounds are present in an amount of approximately 20 to approximately 40% by weight based on the total weight of the composition.

19. The dental restoration material of claim 14, wherein said silanized dental filler is present in an amount of approximately 60 to approximately 80% by weight.

20. The dental restoration material of claim 14, wherein the particle sizes of said silanized dental filler are between 0.01 and 30 micrometers.

21. The dental restoration material according to claim 14, wherein said filler is a mixture of barium alumimum silicate glass with an average particle size of between approximately 3 and 10 micrometers and a finely divided colloidal silica with an average particle diameter between approximately 30 and 100 nm.

22. The dental restoration material of claim 21, wherein the major part of said mixture is said silica.

23. The dental restoration material of claim 14, which contains a silica-gel with an average particle diameter of between approximately 20 and approximately 200 nm as said filler.

24. The dental restoration material of claim 14, wherein the major part of said filler is a silica-gel.

* * * * *